(12) United States Patent
White et al.

(10) Patent No.: US 8,742,180 B1
(45) Date of Patent: Jun. 3, 2014

(54) PROCESS CONTROL WITH RAMAN SPECTROSCOPY

(71) Applicant: Lyondell Chemical Technology, L.P., Houston, TX (US)

(72) Inventors: Daniel F. White, Houston, TX (US); Brian A. Salisbury, Beach City, TX (US); Jenny M. Oran Osment, Humble, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 13/675,503

(22) Filed: Nov. 13, 2012

(51) Int. Cl.
*C07C 29/141* (2006.01)
*C07C 29/16* (2006.01)
*C07C 29/44* (2006.01)
*C07C 29/48* (2006.01)
*C07C 31/20* (2006.01)

(52) U.S. Cl.
CPC .................. *C07C 29/16* (2013.01); *C07C 29/44* (2013.01); *C07C 29/48* (2013.01); *C07C 31/207* (2013.01)
USPC .......................................... 568/860; 568/861

(58) Field of Classification Search
CPC ........ C07C 29/16; C07C 29/44; C07C 29/48; C07C 31/207
USPC ................................................. 568/860, 861
See application file for complete search history.

(56) References Cited

U.S. PATENT DOCUMENTS

| | | | |
|---|---|---|---|
| 3,044,850 A | 7/1962 | Denton | |
| 3,274,121 A | 9/1966 | Schneider | |
| 4,064,145 A | 12/1977 | Taylor | |
| 4,238,419 A | 12/1980 | Matsumoto | |
| 4,306,087 A | 12/1981 | Matsumoto | |
| 4,567,305 A | 1/1986 | Matsumoto | |
| 5,414,138 A | 5/1995 | Omatsu et al. | |
| 6,127,584 A | 10/2000 | Zajacek | |
| 6,225,509 B1 | 5/2001 | Dubner | |
| 6,420,595 B1 | 7/2002 | Hallinan | |
| 7,271,295 B1 | 9/2007 | White | |
| 7,279,606 B1 | 10/2007 | White | |
| 7,294,602 B1 | 11/2007 | White | |
| 7,505,127 B2 | 3/2009 | Marrow | |
| 2010/0292514 A1 | 11/2010 | White | |
| 2012/0130119 A1 | 5/2012 | Salisbury | |

FOREIGN PATENT DOCUMENTS

| | | |
|---|---|---|
| EP | 0627399 A1 | 12/1994 |
| WO | WO2008121194 A1 | 10/2008 |

OTHER PUBLICATIONS

PCT/US2013/069690 International Search Report & Written Opinion mailed Feb. 26, 2014.

*Primary Examiner* — Elvis O Price

(57) ABSTRACT

Embodiments of the present disclosure include methods of effecting process control in a reaction system for the production of 1,4-butanediol, the method including determining at least one property of a sample from the reaction system using Raman spectroscopy, and adjusting at least one parameter of the reaction system in response to the at least one determined property. Embodiments may also include methods of producing 1,4-butanediol, the method including reacting allyl alcohol with carbon monoxide and hydrogen in the presence of a solvent and a catalyst to produce a reactor fluid, sampling the reaction, determining at least one property of the sample using Raman spectroscopy, and adjusting the reaction in response to the at least one determined property.

20 Claims, 2 Drawing Sheets

PROCESS CONTROL WITH RAMAN SPECTROSCOPY

FIELD

Embodiments disclosed herein relate to systems and methods for increasing the production efficiency of 1,4-butanediol. More specifically, embodiments disclosed herein relate to systems and methods for monitoring the feed and effluent streams during the production of 1,4-butanediol. More specifically still, embodiments disclosed herein relate to systems and methods for monitoring the feed and effluent streams during the production of 1,4-butanediol using Raman spectroscopy.

BACKGROUND

This section introduces information from the art that may be related to or provide context for some aspects of the technique described herein and/or claimed below. This information is background facilitating a better understanding of that which is disclosed herein. This is a discussion of "related" art. That such art is related in no way implies that it is also "prior" art. The related art may or may not be prior art. The discussion is to be read in this light, and not as admissions of prior art.

In the production of 1,4-butanediol the reactor feeds and effluents are monitored in order to optimize production, as well as ensure the operation complies with safety regulations. Typically, the feeds and effluents are monitored using either gas chromatography and/or mass spectrometry.

A gas chromatograph may analyze the inlet and outlet reactor feed and effluent streams. When using a gas chromatograph, a physical sample of the fluid is extracted from the system and delivered to the gas chromatograph. During the extraction and transferring the sample from the system to the gas chromatograph, chemical changes may occur prior to analysis. Additionally, gas chromatography may require long testing times, such as up to and exceeding 15 minutes. Thus, there is a lag time between conditions in the system when the sample was taken and when the results are obtained.

Accordingly, there exists a continuing need for systems and methods for monitoring the properties of feeds and effluents in 1,4-butanediol production. The presently disclosed technique is directed to resolving, or at least reducing, one or all of the problems mentioned above. Furthermore, the art is always receptive to improvements or alternative means, methods and configurations.

SUMMARY

In one aspect, embodiments disclosed herein relate to methods of effecting process control in a reaction system for the production of 1,4-butanediol, the method including determining at least one property of a sample from the reaction system using Raman spectroscopy. The methods further including adjusting at least one parameter of the reaction system in response to the at least one determined property.

In another aspect, embodiments disclosed herein relate to methods of producing 1,4-butanediol, the method including reacting allyl alcohol with carbon monoxide and hydrogen in the presence of a solvent and a catalyst to produce a reactor fluid. The methods may further include sampling the reaction, determining at least one property of the sample using Raman spectroscopy, and adjusting the reaction in response to the at least one determined property.

The above presents a simplified summary of the present disclosure to provide a basic understanding of some aspects of the invention. This summary is not an exhaustive overview of the invention. It is not intended to identify key or critical elements or to delineate the scope of the invention. Its sole purpose is to present some concepts in a simplified form as a prelude to the more detailed description that is discussed later.

BRIEF DESCRIPTION OF DRAWINGS

The claimed subject matter may be understood by reference to the following description taken in conjunction with the accompanying drawings, in which like reference numerals identify like elements, and in which:

Figure 1:
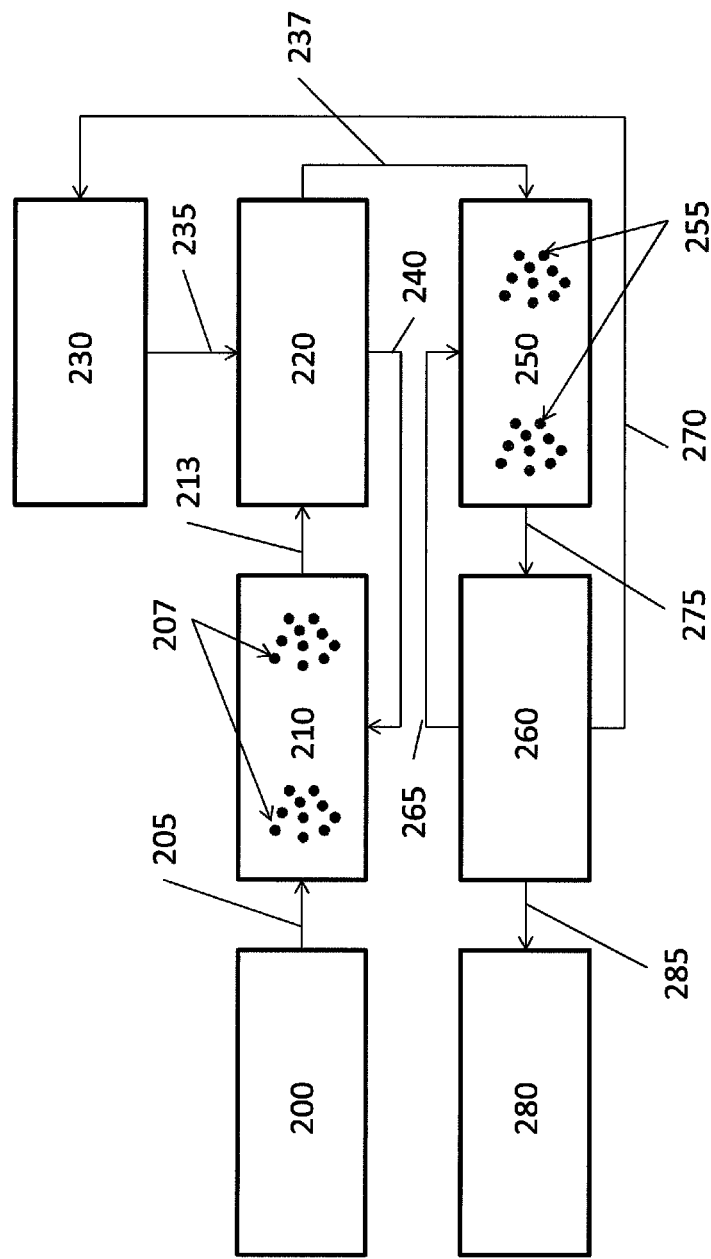
FIG. 1 is a schematic representation of a system for converting allyl alcohol to 1,4-butanediol according to embodiments of the present disclosure.

While the subject matter claimed below is susceptible to various modifications and alternative forms, the drawings illustrate specific embodiments herein described in detail by way of example. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

One or more specific embodiments of the present invention will be described below. The present invention is not limited to the embodiments and illustrations contained herein, but include modified forms of those embodiments including portions of the embodiments and combinations of elements of different embodiments as come within the scope of the appended claims. In the development of any such actual implementation, as in any engineering or design project, numerous implementation-specific decisions must be made to achieve the developers' specific goals, such as compliance with system-related and business related constraints, which may vary from one implementation to another. Moreover, such a development effort might be complex and time consuming, but would nevertheless be a routine undertaking of design, fabrication, and manufacture for those of ordinary skill having the benefit of this disclosure.

In one aspect, embodiments disclosed herein relate to systems and methods for increasing the production efficiency of 1,4-butanediol. In other aspects, embodiments disclosed herein relate to systems and methods for monitoring the feed and effluent streams during the production of 1,4-butanediol. In still other aspects, embodiments disclosed herein relate to systems and methods for monitoring the feed and effluent streams during the production of 1,4-butanediol using Raman spectroscopy.

Embodiments of the present disclosure may allow for the more efficient production of 1,4-butanediol, which is a common intermediate ingredient used in the production of various industrial and commercial products. The 1,4-butanediol is reacted to make, for example, engineering plastics, polyurethane systems, and is used as a carrier solvent in inks and cleaning agents.

Raman spectroscopy is known, for instance, see U.S. Pat. No. 7,505,127. It is an established analytical technique for chemical characterization, quantification, and identification. Raman spectroscopy provides information on molecular vibrational-rotational states. Raman shifts occur when radiation impinges on a molecule causing a change in the polarizability of the electron cloud of that molecule. In Raman, the molecule is excited from ground state to a virtual state and emits a photon as it relaxes back to a different vibrational or rotational state from where it started. Most of the incident radiation is elastically scattered (Rayleigh scatter) at the same wavelength as the source, however a small portion is inelastically scattered. This inelastic scatter is Raman scatter and includes both Stokes (emitted scatter has less energy than absorbed photon) and anti-Stokes (emitted scatter has more energy than absorbed photon) scatter. These differences in energy between the original state and this new state lead to a shift in the emitted photon's frequency away from the excitation wavelength—this is the Raman shift. Raman spectra are typically shown as plots of intensity (arbitrary units) versus Raman shift, which is often expressed in wavenumbers. In spectroscopy, wavenumbers are expressed as inverse centimeters ($cm^{-1}$).

The instrumentation used to collect and process Raman data is composed of a Raman spectrometer system, a transmittance system, a control loop, and a processor. The Raman spectrometer system contains a light source, a filter for Rayleigh scatter rejection, a monochromator, and a detector. The light source provides the excitation radiation that is transmitted through the probe to the sampling area. Scattered radiation is collected back through the probe, filtered of Rayleigh scatter, and dispersed via a monochromator. The dispersed Raman scatter is then imaged onto a detector and subsequently processed within the processor.

Typically, the light source is a visible laser, such as a frequency-doubled Nd:YAG laser (532 nm), a helium-neon laser (633 nm), or a solid-state diode laser (such as 785 nm). The laser can be pulsed or continuous wave (CW), polarized as desired or randomly polarized, and preferably single-mode. Typical excitation lasers will have 100 to 400 mW power (CW), although lower or higher power can be used as desired. Light sources other than lasers can be used, and wavelengths and laser types and parameters other than those listed above can also be used.

The excitation radiation can be delivered to the probe, and the scattered radiation collected from the probe by any convenient means known in the art, such as conventional beam manipulation optics or fiber optic cables generally designated. For an on-line process measurement, it is particularly convenient to deliver the excitation radiation and collect the scattered radiation through fiber optic cables. It is a particular advantage of Raman spectroscopy that the excitation radiation typically used is readily manipulated fiber optically, and thus the excitation source can be positioned remotely from the sampling region.

The scattered radiation is collected and dispersed by any convenient means known in the art, such as a fiber optic probe. The collected scattered radiation is filtered to remove Rayleigh scattering and then frequency (wavelength) dispersed using a suitable dispersive element, such as a blazed grating or a holographic grating, or interferometrically (e.g., using Fourier transforms). The grating can be fixed or scanning, depending upon the type of detector used. The monochromator can be any such dispersive element, along with associated filters and beam manipulation optics.

The dispersed Raman scattering is imaged onto a detector. Typical detectors include array detectors generally used with fixed-dispersive monochromators, such as diode arrays or charge coupled devices (CCDs), or single element detectors generally used with scanning-dispersive monochromators or FT-based spectrometers, such as lead sulfide detectors and indium-gallium-arsenide detectors. In the case of array detectors, the detector is calibrated such that the frequency (wavelength) corresponding to each detector element is known. The detector response is delivered to the processor that generates a set of frequency shift, intensity (x,y) data points which constitute the Raman spectrum.

During the production of 1,4-butanediol, multiple steps may be used. In certain systems, propylene oxide is used as the primary feed stock; however, those ordinarily skilled in the art will appreciate that other feed stocks may also be used, such as, for example, acetylene. To explain the use of Raman spectroscopy in the production of 1,4-butanediol, an exemplary system using a feed stock of allyl alcohol is discussed in detail. The allyl alcohol is hydroformylated to 4-hydroxybutyraldehyde. Hydrogenation of the 4-hydroxybutyraldehyde then results in 1,4-butanediol. This process is shown below:

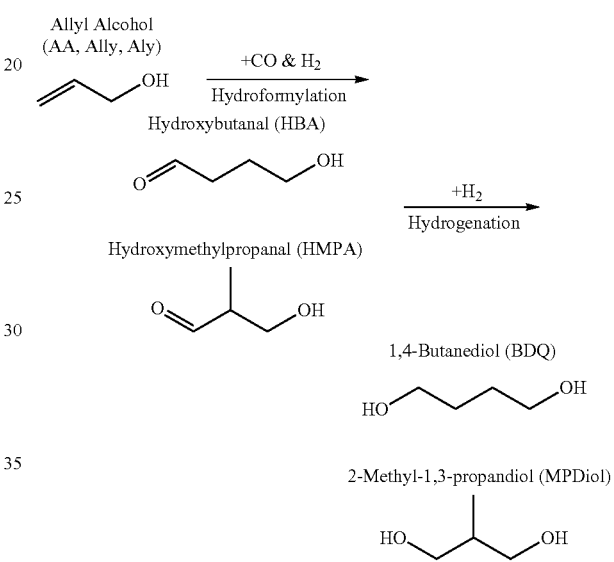

The allyl alcohol may come from propylene oxide, as shown below:

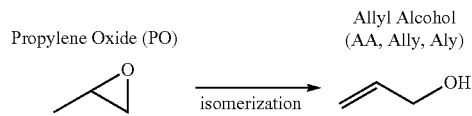

In the process, allyl alcohol may be produced by the isomerization of propylene oxide through either a slurry-phase or a gas-phase (i.e., vapor-phase) process. Examples of slurry-phase processes may be found in, for example, U.S. Pat. No. 3,274,121, while examples of gas-phase processes may be found in, for example, U.S. Pat. No. 3,044,850.

In other embodiments, the allyl alcohol may come from propylene, as shown below, or from other processes, such as, for example, from glycerol (not shown).

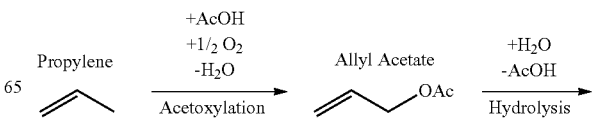

Allyl Alcohol (AA, Ally, Aly)

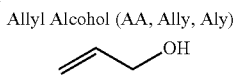

In this process, allyl alcohol can be produced by the acetoxylation of propylene to produce allyl acetate followed by hydrolysis of the allyl acetate to form allyl alcohol.

Referring to FIG. 1, a schematic representation of a system for converting allyl alcohol to 1,4-butanediol according to an embodiment of the present disclosure is shown. The process of producing 1,4-butanediol from allyl alcohol includes hydroformylating the allyl alcohol in the presence of a solvent and a catalyst and then hydrogenating the products of the hydroformylation to produce, among other potential products, 1,4-butanediol.

Initially, an allyl alcohol feed 205 is transferred either from a stock tank 200 or directly fed from an allyl alcohol production line. Whether fed directly from an allyl alcohol production process or from the stock tank 200, the allyl alcohol feed 205 is transferred to a hydroformylation reactor 210. Hydroformylation reactor 210 may be configured to hydroformylate the allyl alcohol into hydroxybutanal (for example, 4-hydroxybutyraldehyde). During the hydroformylation, other products, such as hydroxymethylpropanal (3-hydroxy-2-methylpropionaldehyde) may also be produced.

The hydroformylation catalyst used in hydroformylation reactor 210 may vary according to the specific requirements of the 1,4-butanediol process. In one embodiment, the hydroformylation catalyst 207 may include a rhodium complex with a phosphine ligand. For example, in a particular embodiment, the hydroformylation catalysis may include a rhodium complex and a 2,3-O-isopropylidene-2,3-dehydroxy-1,4-bis [bis(3,5-de-n-alkylphenyl)phosphine]butane. Additionally, suitable rhodium complexes may contain rhodium attached to ligand groups. In other embodiments, other hydroformylation catalysts may be used, such as trialkyl phosphine ligands having at least 2 methyl groups, disphosphine ligands, diphosphine ligands, etc. Examples of hydroformylation catalysts and catalyst systems that may be used according to embodiments of the present disclosure are discussed in U.S. Pat. Nos. 4,064,145, 4,238,419, 4,567,305, 6,127,584, 4,306,087, 6,225,509, and 7,271,295, and are hereby incorporated by reference herein.

A reaction solvent (not shown) may also be required in hydroformylation reactor 210. Any solvent may be used that is capable of solubilizing the rhodium complex and which is not reactive to the hydroxyaldehydes that are produced during hydroformylation. Examples of suitable solvents may include, for example, any organic solvent that has low or minimal solubility in water, such as, $C_5$ to $C_{20}$ aliphatic hydrocarbons, $C_6$ to $C_{20}$ aromatic hydrocarbons, alcohols, ethers, and mixtures thereof. In one embodiment, the solvent may include toluene, cyclohexane, methyl t-butyl ether, and mixtures thereof.

Reaction conditions within hydroformylation reactor 210 may be configured to favor the formation of hydroxybutanal over hydroxymethylpropanal. Reaction conditions may occur in a temperature range between from about 20° C. to about 102° C. In certain embodiments, the temperature range may be between about 45° C. to about 85° C., and in still further embodiments, the temperature may be about 65° C. The reaction conditions may further include various pressure ranges, such as a pressure ranging between about 20 psi to about 600 psi. In certain embodiments, the pressure may range between about 30 psi to about 400 psi, and in still further embodiments, the pressure may range between about 35 psi and about 135 psi. The starting concentration of the reaction solvent to feed basis may be in a range between about 5 to about 40 percent by weight allyl alcohol to solvent, and in certain embodiments, may be lower. In one embodiment, the reaction solvent to feed basis may be in a range between about 5 to about 20 percent by weight ("wt %") allyl alcohol to solvent.

The allyl alcohol feed stream 205 is introduced into hydroformylation reactor 210 and reacted with gases, such as carbon monoxide and hydrogen in the presence of the hydroformylation catalyst 207 until a desired portion of the allyl alcohol has reacted. For example, in certain embodiments, the allyl alcohol is reacted until between about 60% and about 99% of the allyl alcohol has been reacted. The time the allyl alcohol will be required to react may vary, but in certain embodiments may be between about 1 and about 4 hours, and in particular embodiments may be about 2 hours.

After the allyl alcohol has been reacted to produce hydroxybutanal, as well as other less desirable compounds, effluent stream 213, containing hydroxybutanal, is transferred from the hydroformylation reactor 210 to a catalyst extractor 220. The hydroxybutanal may be separated from the catalysts and solvents in the effluent stream 213 through the use of, for example, water extraction. In one embodiment, water may be provided from a water feed source 230 through a water transfer line 235. The catalyst extractor 220 may use various components to extract the hydroxybutanal from the catalysts and solvents in the effluent stream 213, such as, for example, mixer-settlers, pack or tray-based extraction columns, rotating disk contactors, and/or settling tanks. The hydroxybutanal and hydroxymethylpropanal are soluble in the water phase and are thus separated from the solvent in the organic phase.

After the catalysts and solvents are extracted from the effluent stream 213 using catalyst extractor 220, the recovered catalysts and solvents may recycled back to hydroformylation reactor 210 via recycle transfer line 240. The catalyst extractor 220 also results in a recovered products effluent stream 237, which may include both hydroxybutanal and hydroxymethylpropanal.

To produce 1,4-butanediol, the hydroxybutanal is hydrogenated in a hydrogenation reactor 250. In the hydrogenation reactor 250, the hydroxybutanal is reacted in the presence of hydrogen to produce 1,4-butanediol. In addition to hydrogen, hydrogenation reactor 250 includes a hydrogenation hydrogenation catalyst 255. Examples of suitable hydrogenation hydrogenation catalysts 255 may include, for example, various Group VIII metals, such as nickel, cobalt, ruthenium, platinum, and palladium, as well as copper, zinc and chromium mixtures, and alloys thereof. In certain embodiments, nickel catalysts may be preferable, such as Raney®-type nickel and fixed bed nickel catalysts. The water supplied with the recovered products effluent stream may be a sufficient solvent, however, in certain embodiments, additional water may be added to hydrogenation reactor 250.

The reaction conditions in hydrogenation reactor 250 may vary based on the properties of the products effluent stream, which contains the hydroxybutanal. In certain embodiments, the temperature in hydrogenation reactor 250 may be between about 60° C. and about 200° C. In other embodiments, the temperature may be in a range between about 80° C. and about 140° C., while in a particular embodiment, the temperature may be about 100° C. The pressure within hydrogenation reactor 250 may also vary depending on the properties of the products effluent stream. In one embodiment, the pressure may be in a range between about 200 psi and about 1000 psi, in a range between about 300 and about 1000 psi, and in a particular embodiment the pressure may be about 750 psi. The time that the hydroxybutanal is reacted in hydrogenation reactor 250 may vary, but in certain embodiments may be between about 1 and about 10 hours, and in particular embodiments may be about 2 hours.

The hydrogenation of the hydroxybutanal results in the conversion of the hydroxybutanal into 1,4-butanediol. The hydrogenation reactor effluent 275, which contains the 1,4-butanediol, as well as other products, such as 2-methyl-1,3-propandiol, water, and residual catalyst may then transferred to a separator 260. The separator 260 may include various distillation columns that allow for the separation of the hydrogenation catalysts 255 and the water from the desired products, e.g., 1,4-butanediol and 2-methyl-1,3-propandiol. The water may be recycled back to the water feed source 230 through a transfer line 270. Similarly, the hydrogenation catalyst 255 may be recycled from the separator 260 to the hydrogenation reactor 250 through a transfer line 265.

The separator 260 product effluent stream 285, containing the desired products, such as the 1,4-butanediol and 2-methyl-1,3-propandiol may then be transferred to discrete storage tanks 280 for sale or use in the manufacture of other desired products.

During the hydroformylation of the allyl alcohol into the branched and linear hydroxyaldehyes, control of the conversion process is necessary to ensure high selectivity of the product, as well as ensure reaction stability and prevent catalyst loss. As described above, the hydroformylation is conventionally monitored using gas chromatography and/or mass spectrometry.

In addition to or instead of gas chromatography and/or mass spectrometry, embodiments of the present disclosure may use Raman spectroscopy and/or combinations of Raman spectroscopy and infrared spectroscopy to determine the properties of the allyl alcohol feed 205, the conditions in hydroformylation reactor 210, and/or the properties of the hydroformylation reactor 210 effluent 213. To determine the properties of the allyl alcohol feed 205, the conditions in hydroformylation reactor 210, and/or the properties of the hydroformylation reactor 210 effluent 213, a sample may be taken from a hydroformylation reactor 210 inlet, outlet, reactor vessel, transfer line, or at any other point in hydroformylation reactor 210. In one embodiment, a liquid probe may be inserted into an inlet or outlet, or directly into the body of a portion of the hydroformylation reactor 210 in order to procure a sample of the slurry in the reactor. As used herein, the term sample does not necessitate extracting a fluid from any component of the process, rather, the term sample refers to gathering data about the fluid from a component of the process.

Depending on the type of spectroscopy being used, the probe may be a near-infrared gas probe (when infrared spectroscopy is being used). Examples of gas probes that may be used for infrared spectroscopy are described in U.S. Pat. No. 6,420,595, which is hereby incorporated by reference herein.

In the case of Raman spectroscopy, the gas or liquid probe may include a sampling probe having an outer sleeve formed from, for example, stainless steel, or other metal and metal alloys that resist corrosion and abrasion. The sampling probe may include a sapphire window, or lens at a distal end of the probe, and may be configured to work at various wavelengths. Inside the probe, at least two fiber optic cables may be mounted, a first fiber optic cable attached to a laser excitation source for illuminating the sampling area, and a second fiber optic cable that is configured to collect the scattered light and transmit the energy to a spectrograph. The spectrograph may then be used to interpret the collected data to determine the composition of the sample.

Based on the properties of the sample, the conditions of the hydroformylation reactor 210 may be adjusted, if required, to optimize for the production of a particular product. Examples of properties that may be adjusted include, for example, the temperature of one or more components of hydroformylation reactor 210, the pressure in one or more components of hydroformylation reactor 210, a flow rate of a fluid between various components of hydroformylation reactor 210, the flow rate of allyl alcohol into hydroformylation reactor 210, the time the allyl alcohol is allowed to react in hydroformylation reactor 210, the carbon monoxide flow to hydroformylation reactor 210, a catalyst/toluene recycle flow rate to hydroformylation reactor 210, etc. Additionally, the determined properties of the sample may be used to adjust a property of a catalyst or solvent, including adjusting the concentration and/or the composition of the catalyst within hydroformylation reactor 210. For example, the composition of the catalyst could be adjusted for the catalyst's various phosphine ligand components.

Those of ordinary skill in the art having benefit of the present disclosure appreciate that infrared and/or Raman spectroscopy techniques, such as those described above, may also be used at other points in the allyl alcohol to 1,4-butanediol production process. For example, infrared and/or Raman spectroscopy may be used to determine the properties of a sample of a feed 205 of allyl alcohol being introduced into hydroformylation reactor 210 or an effluent 213 of hydroformylation reactor 210. Samples may also be taken in the catalyst extractor 220 or in the hydrogenation reactor 250. In either case, the sample may be taken on a feed line 213/237 into the catalyst extractor 220 or the hydrogenation reactor 250, or from one or more of the effluent streams 275 discharged from the catalyst extractor 220 or the hydrogenation reactor 250. Similarly, the operating conditions of either the catalyst extractor 220 or the hydrogenation reactor 250 may be adjusted to further optimize for the production of 1,4-butanediol.

In certain embodiments, the samples may be analyzed online, thereby allowing the results to be obtained more quickly than using off-line methods of taking samples and analyzing the samples in a lab. In such on-line systems, the sampling probe may procure a sample from a desired section of the production process. The sample may be processed by a spectrograph that is directly connected to the sampling probe or, in certain embodiments, the probe may wirelessly transmit the data to a spectrograph. Those of ordinary skill in the having benefit of this disclosure will appreciate that the wireless methods of transmitting data may include, local area network transference, RF transference, Bluetooth® transference and the like.

In certain embodiments, properties of the samples may be determined in real-time or near real-time. As used herein, the terms "real-time" and "near real-time" pertain to processing data and generating outputs within a time not later than the time when the outputs are needed for effective control of a system. The terms "real-time" and "near real-time" are not intended to require that the processing and/or generating of outputs occurs instantaneously.

After analysis of the sample with the spectrograph, the properties of the sample may be displayed or transmitted to an operator, such as a process engineer. The operator may then review the displayed properties of the sample and adjust the production process as discussed above. In certain embodiments, the properties of the fluid may be stored in a database, thereby allowing for the aggregation of data points that may be used to determine, for example, the operating efficiency over time of one or more components of the production process. The aggregation of data may further allow for the more accurate prediction of how a change in one variable of the production process affects the produced products.

Methods of the present disclosure may be used to effect the process control in a reaction system for the production of 1,4-butanediol. The method may include, for example, determining at least one property of a sample from a reaction system using Raman spectroscopy. The reaction system may include any number of reactors, extractors, distillation columns, separators, and storage tanks, as well as all associated transfer lines. In certain embodiments, the sample may be collected from a hydroformylation reactor and/or a hydrogenation reactor. Examples of such components of a reaction system are described above with respect to FIGS. 1 and 2. After determining at least one property of a sample from the reaction system, at least one parameter of the reaction system may be adjusted in response to the at least one determined property.

Examples of properties that may be determined include an allyl alcohol concentration, a hydroxybutanal concentration, a hydroxymethylpropanal concentration, etc. Examples of parameters that may be adjusted include a temperature, pressure, catalyst concentration, catalyst composition and/or a flow rate of any aspect of the reaction system.

In certain embodiments, more than one sample may be collected from more than one location in the reaction system. In such an embodiment, a property of each of the at least two samples may be determined and a parameter of the reaction system may be adjusted in response to the determined properties of the at least two samples. Those of ordinary skill in the art having the benefit of this disclosure will appreciate that in alternative embodiments, any number of samples may be taken and either used independently or aggregated when determining whether to adjust a component of the reaction system.

The sample may be collected by inserting a sample probe into at least one component of the reaction system. The sample probe may then be used to illuminate a fluid in the reaction system and then the probe may be used to collect scattered light from the illuminated sample. Examples of fluids that may be sampled, include liquid and/or gas phase fluids that include allyl alcohol, hydroxybutanal, hydroxymethylpropanal, and/or 1,4-butanediol.

In certain embodiments, the determining of properties of samples taken from the reaction system may occur on-line or in real-time. Thus, the sample may be analyzed in order to determine properties and provide data representative of properties of the sample so that an operator may adjust one or more parameter of the reaction system.

In addition to using Raman spectroscopy, in certain embodiments, infrared spectroscopy may also be used. In such an embodiment, a sample may be analyzed using both Raman spectroscopy and infrared spectroscopy and the results of the analysis may be aggregated to determine one or more properties about the sample.

The present disclosure also provides methods of producing 1,4-butanediol, which may include reacting allyl alcohol with carbon monoxide and hydrogen in the presence of a solvent and a catalyst to produce a reactor fluid. The reaction may then be sampled, such as through the methods described above. After sampling the reaction, at least one property of the sample may be determined using Raman spectroscopy. In certain embodiments, both Raman spectroscopy and infrared spectroscopy may be used to determine the at least one property of the sample. After determining at least one property of the sample, the reaction may be adjusted based on the determined property.

The property that is adjusted may include, for example, a concentration of allyl alcohol, a concentration of carbon monoxide, a concentration of hydrogen, a concentration of a solvent, and/or a concentration of a catalyst.

The method may further include reacting hydroxybutanal with hydrogen in the presence of water and a second catalyst to produce 1,4-butanediol. In certain embodiments, the method may include collecting a second sample from the reacting hydroxybutanal with hydrogen in the presence of water and the second catalyst, determining at least one property of the second sample, and adjusting the reacting in response to the determined property of the second sample.

EXAMPLE

To show that Raman spectroscopy may be used to determine the properties of samples during the hydroformylation or hydrogenation process, a laboratory test was performed on samples of allyl alcohol. In the test, a series of allyl alcohol-toluene solutions were produced having varying concentrations, as depicted in Table 1, below:

TABLE 1

| Standard | Percent Allyl Alcohol |
|---|---|
| 1 | 0.0000 |
| 2 | 0.9965 |
| 3 | 2.0487 |
| 4 | 3.0434 |
| 5 | 5.0054 |
| 6 | 9.8841 |
| 7 | 14.8933 |
| 8 | 19.7040 |

The samples of varying allyl alcohol concentration were analyzed using Raman spectroscopy. In analyzing the samples, 780 nm excitation was used at 100% power through a 50 µm slit. The samples were taken in 28×4 second acquisitions and a calibration curve was plotted using chemometric modeling.

Figure 2:
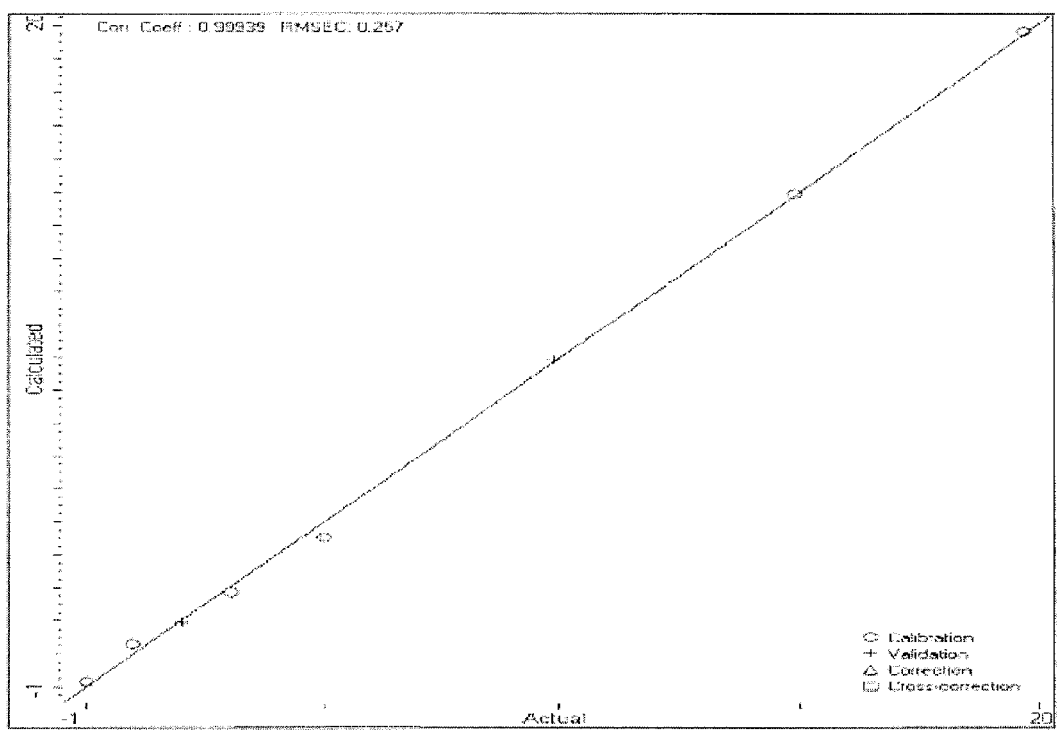
FIG. 2 is a calibration curve for the determination of a weight percent allyl alcohol in toluene in a laboratory test according to embodiments of the present disclosure.

Referring briefly to FIG. 2, the calibration curve of the samples according to embodiments of the present disclosure is shown. The linear nature of the calibration curve demonstrates that Raman spectroscopy may be used to determine a concentration of allyl alcohol in a solution.

Advantageously, embodiments of the present disclosure discussed herein may allow for the more efficient production of products. More specifically, embodiments of the present disclosure may allow for the more efficient production of 1,4-butanediol from allyl alcohol.

Also advantageously, embodiments of the present disclosure may allow the reaction stability in hydroformylation reactors and/or hydrogenation reactors to be increased. By increasing the reaction stability, the production of the desired product may be increased, as well as the overall safety of the process may be increased.

Advantageously, embodiments of the present disclosure may result in minimized catalyst loss. Because more accurate data may be gathered during hydroformylation and hydrogenation, the properties of the respective reactors may be adjusted to minimize the loss of catalyst, thereby improving the profitability of the production process.

Also advantageously, embodiments of the present disclosure may allow for the on-line analysis of samples of hydroformylation and hydrogenation reactors. The on-line analysis may thereby allow for sample properties to be determined in real-time or near real-time, providing for a more accurate understanding of the production process. Because the properties of the samples may be determined in real-time or near real-time, problems with the process that may result in a dangerous condition or inefficient production may be addressed. By increasing the speed with which production process problems are addressed, the production process efficiency may be increased, thereby increasing the profitability of the production process.

Note that not all embodiments will necessarily exhibit any or all of the advantages listed above. Among those embodiments exhibiting one of more of those advantages, not all of them will exhibit them equally.

The following U.S. Letters Patent are hereby incorporated by reference for the purposes cited above as if expressly set forth verbatim herein:

U.S. Pat. No. 4,064,145, entitled "Production of tetrahydrofuran", and issued Dec. 20, 1977, to Celanese Corporation as assignee of the inventor Paul D. Taylor.

U.S. Pat. No. 4,238,419, entitled "Hydroformylation of olefinic compounds", and issued Dec. 9, 1980, to Kuraray Co., Ltd. as assignee of the inventors Mitsuo Matsumoto and Masuhiko Tamura.

U.S. Pat. No. 4,567,305, entitled "Process for continuous hydroformylation of allyl alcohol", and issued Jan. 28, 1986, to Kuraray Company, Ltd. And Daicel Chemical Industries, Ltd. as assignee of the inventors Mitso Matsumoto, Shinichi Miura, Koichi Kikuchi, Masuhiko Tamura, Hidetaka Kojima, Kunio Koga, and Shigeru Yamashita.

U.S. Pat. No. 6,127,584, entitled "Butanediol Production", and issued Oct. 3, 2000, to Arco Chemical Technology, L. P. as assignee of the inventors Joan G. Zajacek and Wilfred P. Shum.

U.S. Pat. No. 4,306,087, entitled "Hydroformylation of olefinic compounds", and issued Dec. 15, 1981, to Kuraray Co., Ltd. as assignee of the inventors Mitsuo Matsumoto and Masuhiko Tamura.

U.S. Pat. No. 6,225,509, entitled "Allyl alcohol hydroformylation", and issued May 1, 2001, to ARCO Chemical Technology, L. P. as assignee of the inventors Walter S. Dubner and Wilfred Po-sum Shum.

U.S. Pat. No. 7,271,295, entitled "Hydroformylation process", and issued Sep. 18, 2007, to Lyondell Chemical Technology, L. P. as assignee of the inventors Daniel. F. White and Walter S. Dubner.

U.S. Pat. No. 6,420,595, entitled "Process control for vinyl acetate manufacture", and issued Jul. 16, 2002, to Millennium Petrochemicals, Inc. as assignee of the inventors Noel Hallinan and Wayne Brtko.

U.S. Patent Publication 2012/0130119, entitled "Vinyl Acetate Production Process", and filed May 24, 2012, in the name of the inventors Brian A. Salisbury, Noel C. Hallinan; Jenny M. Oran Osment, and commonly assigned herewith.

In the event of conflict between one or more of the incorporated patents and the present disclosure, the present specification, including definitions, controls.

While the present disclosure has been described with respect to a limited number of embodiments, those skilled in the art, having benefit of this disclosure, will appreciate that other embodiments may be devised which do not depart from the scope of the disclosure as described herein. Accordingly, the scope of the disclosure should be limited only by the attached claims.

What is claimed:

1. A method of effecting process control in a reaction system for the production of 1,4-butanediol, the method comprising:
   determining at least one property of a sample from the reaction system using Raman spectroscopy; and
   adjusting at least one parameter of the reaction system in response to the at least one determined property.

2. The method of claim 1, further comprising:
   inserting a sample probe into at least one component of the reaction system;
   illuminating a fluid in the reaction system with the probe, and
   collecting scatter light from the illuminated fluid with the probe.

3. The method of claim 1, wherein the determining occurs on-line.

4. The method of claim 1, wherein the determining occurs in real time.

5. The method of claim 1, wherein the sample comprises at least one component selected from a group consisting of allyl alcohol, hydroxybutanal, hydroxymethylpropanal, and 1,4-butanediol.

6. The method of claim 1, wherein the sample is collected from a hydroformylation reactor.

7. The method of claim 1, wherein the sample is collected from a hydrogenation reactor.

8. The method of claim 1, wherein the sample is collected from at least one of a group consisting of an allyl alcohol feed stream, a hydroformylation reactor effluent stream, a catalyst extractor effluent stream, a hydrogenation reactor effluent stream, and a catalyst extractor recycle stream.

9. The method of claim 1, wherein adjusting the parameter comprises adjusting at least one of a group consisting of a temperature, a pressure, an allyl alcohol flow rate, a carbon monoxide flow rate, a hydrogen flow rate, a residence time, a catalyst concentration, a catalyst composition and a catalyst flow rate.

10. The method of claim 1, wherein the property comprises a least one of a group consisting of an allyl alcohol concentration, a hydroxybutanal concentration, a hydroxymethylpropanal concentration, a propanal concentration, and a propanol concentration.

11. The method of claim 1, wherein the determining further comprises determining at least one property of the sample using infrared spectroscopy.

12. The method of claim 1, wherein at least two samples are collected at different locations within the reaction system.

13. The method of claim 12, further comprising determining at least one property of each of the at least two samples, and adjusting the at least one parameter of the reaction system in response to the determined properties of each of the at least two samples.

14. A method of producing 1,4-butanediol, the method comprising:
   reacting allyl alcohol with carbon monoxide and hydrogen in the presence of a solvent and a catalyst to produce a reactor fluid;
   sampling the reaction;
   determining at least one property of the sample using Raman spectroscopy; and
   adjusting the reaction in response to the at least one determined property.

15. The method of claim 14, wherein the adjusting comprises, adjusting at least one of a group consisting of a concentration of the allyl alcohol, a concentration of the carbon monoxide, a concentration of the hydrogen, a concentration of the solvent, and a concentration of the catalyst.

16. The method of claim 14, wherein the determining further comprises determining at least one property of the sample using infrared spectroscopy.

17. The method of claim 14, wherein the collecting comprises, illuminating the reactor fluid, and collecting scatter light from the illuminated reactor fluid.

18. The method of claim 14, wherein the determining comprises determining the at least one property in real-time.

19. The method of claim 14, further comprising reacting hydroxybutanal with hydrogen in the presence of water and a second catalyst to produce 1,4-butanediol.

20. The method of claim 19, further comprising collecting a second sample from the reacting hydroxybutanal with hydrogen in the presence of water and the second catalyst; determining at least one property of the second sample; and adjusting the reacting in response to the determined property of the second sample.

\* \* \* \* \*